(12) United States Patent
Lin

(10) Patent No.: US 12,042,679 B2
(45) Date of Patent: Jul. 23, 2024

(54) AIR PURIFICATION FACE MASK STRUCTURE

(71) Applicant: Jerome Lin, New Taipei (TW)

(72) Inventor: Jerome Lin, New Taipei (TW)

( * ) Notice: Subject to any disclaimer, the term of this patent is extended or adjusted under 35 U.S.C. 154(b) by 574 days.

(21) Appl. No.: 17/316,971

(22) Filed: May 11, 2021

(65) Prior Publication Data

US 2021/0361982 A1     Nov. 25, 2021

(30) Foreign Application Priority Data

May 20, 2020   (TW) ................. 109206247

(51) Int. Cl.
| | | |
|---|---|---|
| A62B 7/10 | (2006.01) | |
| A62B 18/00 | (2006.01) | |
| A62B 18/02 | (2006.01) | |
| A62B 18/08 | (2006.01) | |
| A62B 23/02 | (2006.01) | |
| B01D 46/00 | (2022.01) | |
| B05B 17/06 | (2006.01) | |
| A41D 13/11 | (2006.01) | |

(52) U.S. Cl.
CPC .............. *A62B 7/10* (2013.01); *A62B 18/006* (2013.01); *A62B 18/025* (2013.01); *A62B 18/08* (2013.01); *A62B 18/084* (2013.01); *A62B 23/02* (2013.01); *B01D 46/0049* (2013.01); *B05B 17/06* (2013.01); *A41D 13/1161* (2013.01)

(58) Field of Classification Search
CPC ........... A61M 16/0605; A41D 13/1192; A41D 13/1161; A41D 31/145; A41D 13/11; A41D 2500/30; A62B 7/10; A62B 23/025; A62B 18/025
See application file for complete search history.

*Primary Examiner* — Ophelia A Hawthorne
(74) *Attorney, Agent, or Firm* — Ian Oglesby

(57) ABSTRACT

The air purification face mask structure of the present invention, which includes a body, a fan, a filter, an outer cover, an air deflector, an ultrasonic vibration device, a face mask body and a strap, in which external air is guided into the face mask by the fan and the air deflector, and a solution like an enzyme or essential oil in a container is converted into an atomized state by the ultrasonic vibration device for spraying towards the mouth and the nose of a user, thereby achieving anti-bacterial and anti-inflammation effects.

2 Claims, 3 Drawing Sheets

AIR PURIFICATION FACE MASK STRUCTURE

BACKGROUND OF THE INVENTION a) Field of the Invention

The present invention relates to an air purification face mask structure, and more particularly to an air purification face mask structure for holding out air pollution, which has anti-bacterial, anti-inflammation and anti-oxidation effects.

b) Description of the Prior Art

Nowadays, as the air quality deteriorates gradually, the air is filled with airborne particulates which are harmful to the human body, and air pollution is already one of the lethal factors to the general public. The culprit of air pollution is mainly PM2.5 present in the air, in which the size of PM2.5 is approximately ½8 of the diameter of hair or ⅓ of a red blood cell. Although PM2.5 cannot be seen by naked eye, it can easily enter into the human body and invade the pulmonary alveoli, infiltrate into the blood circulation system and cause various diseases including asthma, allergies or dermatitis, and even lung cancer or liver cancer, which make health deteriorate from long-term accumulation in the human body.

Currently, one of the main method of keeping away air pollution for the general public is to wear a face mask. Although a general face mask can block and allow some larger particulate matter or organic matter to become adsorbed, when the particulate matter or organic matter becomes adsorbed to a certain level, the face mask becomes ineffective. Moreover, a general face mask is only 30%-80% effective for blocking PM2.5, and cannot completely filter the fine particulate matter in PM2.5, and the general face mask is mostly disposable and cannot be used repeatedly and also has the disadvantage of being stifling. Most importantly, a general face mask cannot achieve the purpose of eliminating bacteria or virus; accordingly, the provision of an innovative hardware design which not only has the effects of eliminating airborne particulates and dust mites as that a traditional face mask, but also achieves anti-bacterial and anti-inflammation effects, is an issue which requires to be overcome and solved with continued efforts by manufacturers and developers for face mask structure related industries.

SUMMARY OF THE INVENTION

The primary object of the present invention is to provide an air purification face mask structure for holding out air pollution, which has anti-bacterial, anti-inflammation and anti-oxidation effects, by internally providing a hardware design including a fan and an air deflector in an air purification face mask structure, effectively using the fan to guide the air outside the air purification face mask structure to the mouth and nose of a user, and guide the air exhaled by the user from a discharge port to outside of the air purification face mask structure to enable breathing in a separate manner, thereby achieving advantages such as anti-bacterial and anti-inflammation effects, as well as enhancing gas circulation in an internal portion of the air purification face mask structure.

DETAILED DESCRIPTION OF THE PREFERRED EMBODIMENTS

Figure 1:
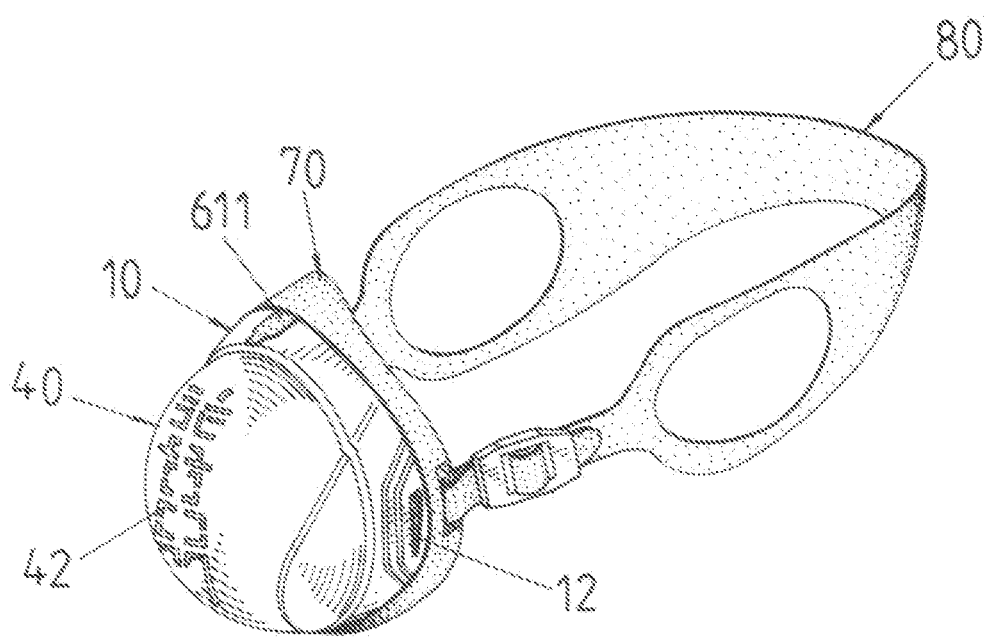
FIG. 1 shows an air purification face mask structure schematic view of the present invention.
Figure 2:
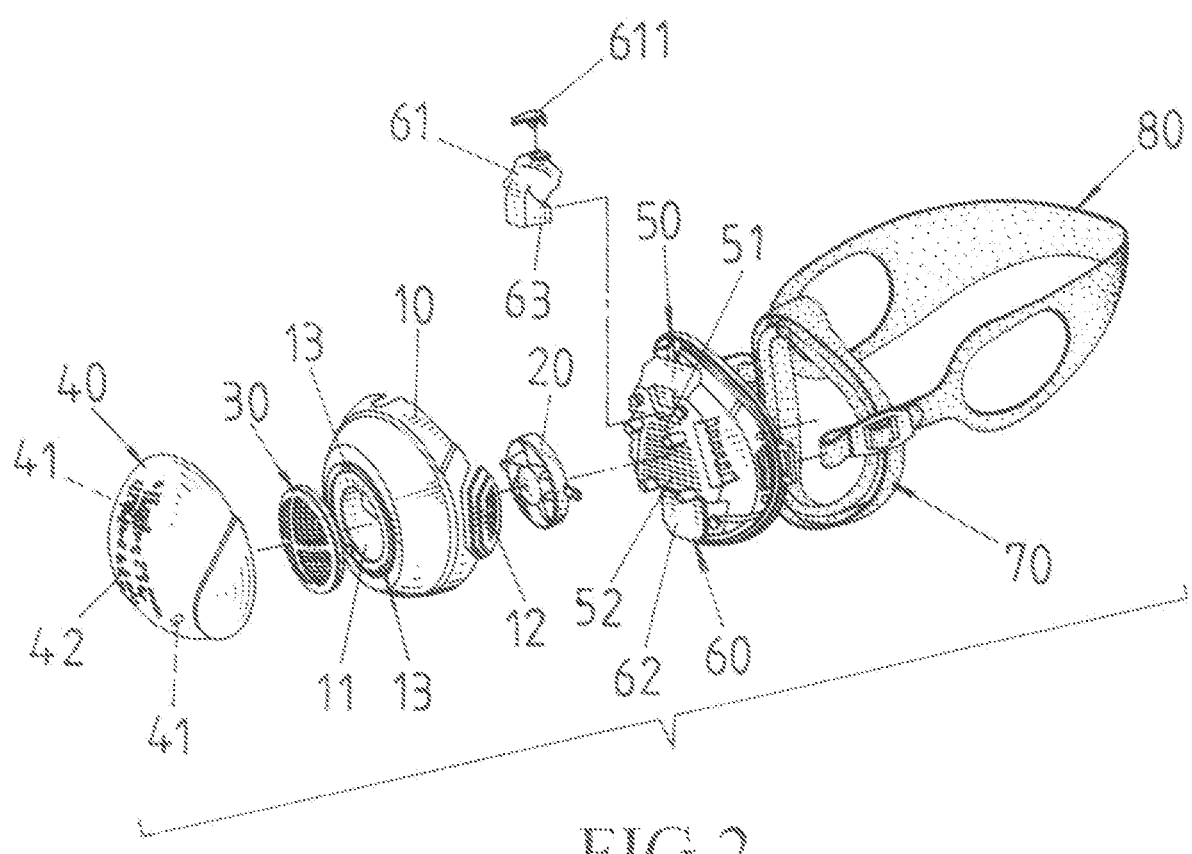
FIG. 2 shows an air purification face mask structure exploded view of the present invention.

Referring to FIG. 1 to FIG. 6, the air purification face mask structure of the present invention comprises a body 10, a fan 20, a filter 30, an outer cover 40, an air deflector 50, an ultrasonic vibration device 60, a face mask 70 and a strap 80, wherein the body 10 is in an annular shape in appearance and can be made of materials such as silicone or an elastic fabric, a central part thereof is provided with an opening 11, adequate positions on two sides thereof are respectively provided with one discharge port 12, gases exhaled from the mouth or nose of a face mask user can be discharged outside of the face mask via the discharge ports 12, and an adequate position on a front edge of the body 10 has at least one joining portion 13.

The fan 20 is mounted in the body 10; the filter 30 is coveringly provided at the opening 11 of the body 10, the filter 30 has another surface thereof being filter cotton (not shown in the drawings), the filter 30, in combination with the filter cotton, is capable of filtering out particulate matter and dust mites harmful to the human body.

The outer cover 40 is provided at a front end of the body 10, an adequate position on an inner side of the outer cover 40 has at least one joining portion 41, the joining portion 41 of the outer cover 40 is joined with the joining portion 13 of the body 10, so as to enable the outer cover 40 and the body 10 to be joined and integrated as a whole, and the joining portion 41 of the outer cover 40 and the joining portion 13 of the body 10 are one of the modes including a magnet, a clasp or a button, in which the mode of magnets is presented in the embodiment of the patent. The outer cover 40 is provided thereon with an air inlet 42, and the mode of a slit is presented in the embodiment of the patent. External air enters into the body 10 from the air inlet 42 of the outer cover 40 and via the filter 30, so as to enable the user to breathe.

Figure 3:
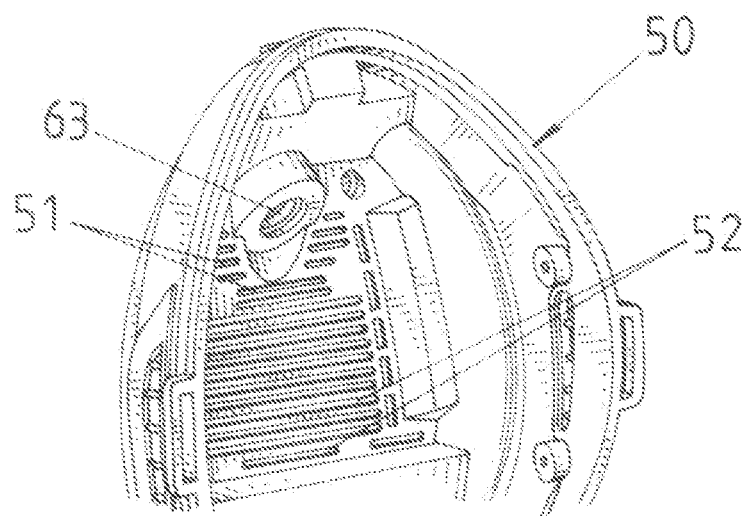
FIG. 3 shows an air purification face mask structure internal structural drawing of the present invention.
Figures 4, 5:
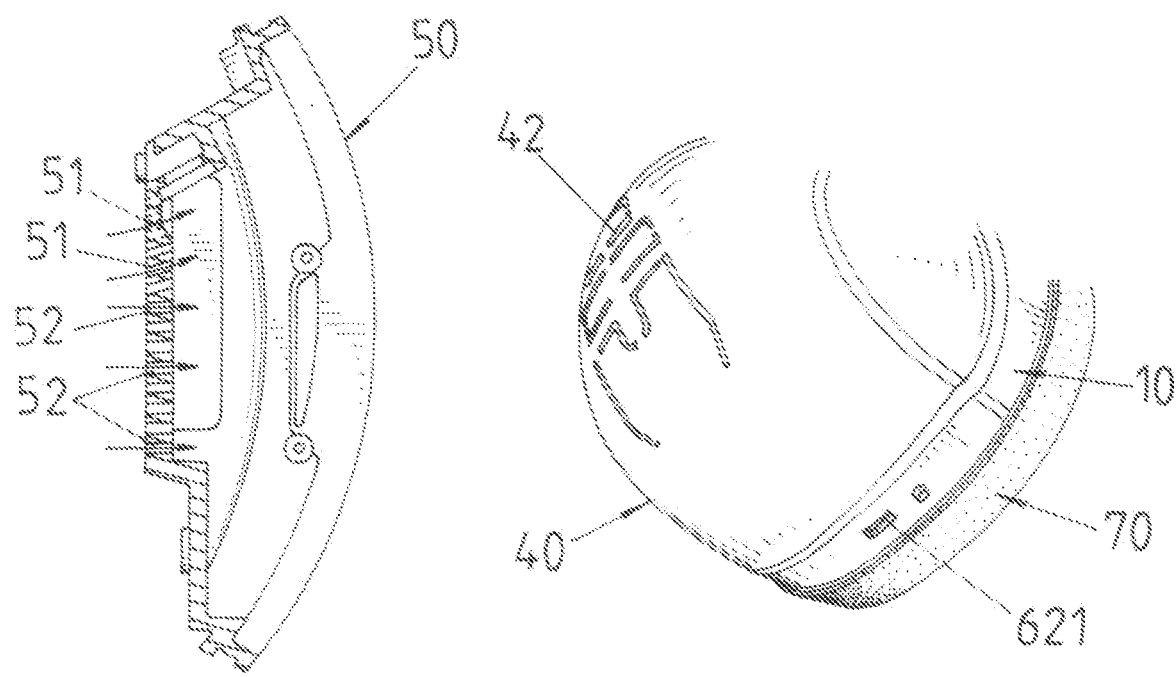
FIG. 4 shows an air purification face mask structure cross-sectional view of the present invention.
FIG. 5 shows an air purification face mask structure bottom schematic view of the present invention.
Figure 6:
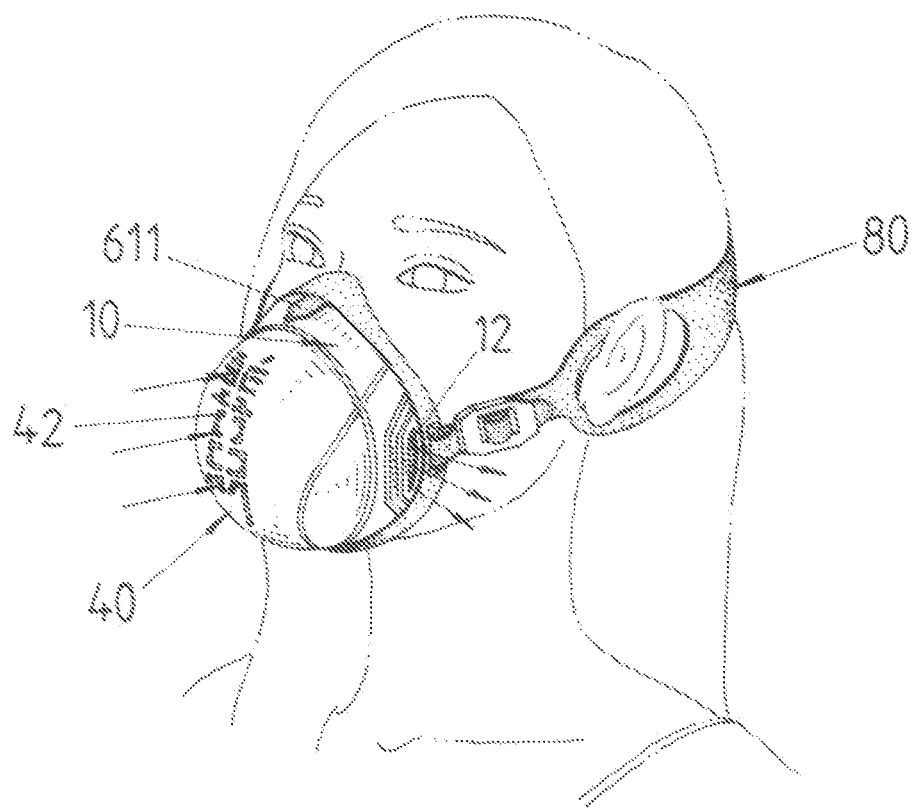
FIG. 6 shows an air purification face mask structure schematic view of an embodiment of the present invention.

The air deflector 50 is engagingly fitted in the body 10, as can be appreciated from FIG. 3, the air deflector 50 has an upper half portion thereof provided with a plurality of first guide holes 51, and a lower half portion thereof provided with a plurality of second guide holes 52; it can be appreciated from FIG. 4 that the plurality of first guide holes 51 are slanted upwards to form an angle with a horizontal plane, when external air passes through the fan 20 and is guided into the body 10, the air current can be blown to the nose and the mouth of the face mask user for breathing via the oblique first guide holes 51; the plurality of horizontal second guide holes 52 are horizontal, and gases exhaled from the nose and the mouth of the face mask user are directly discharged externally from the discharge ports 12 of the body 10 via the horizontal second guide holes 52, so as to enable breathing in a separate manner.

The ultrasonic vibration device 60 is an atomizer, but not limited to an atomizer, mounted in an adequate position on the air deflector 50, the ultrasonic vibration device 60 comprises: a container 61, a circuit board 62 and a nozzle 63, in which the container 61 is stored therein with a solution of an enzyme or essential oil, or a mixture of both, an opening on an upper end of the container 61 is provided with a lid 611, and the user can open the lid 611 to fill in an enzyme or essential oil from the opening; the circuit board 62 has one end thereof connected to a circuit of the fan 20 and another end thereof connected to a charging socket 621 (as shown in FIG. 5), which can be connected to an electric supply to provide a power supply; the nozzle 63 is mounted on the container 61 and is electrically connected to the circuit board 62, the nozzle 63 is capable of atomizing the enzyme or essential oil in the container 61 and spraying the same towards the nose and the mouth of the user, and is also capable of enhancing the effect of hydrogen water in the enzyme, so as to enhance the anti-oxidation effect of anthocyanin in the enzyme.

The face mask body 70 is in an annular shape and made of a silicone material, provided at a back end of the body 10, so that when the user wears the face mask, the face mask body 70 can be tightly fitted to the nose of the user.

The strap 80 is mounted on the body 10 by means of perforations of the face mask body 70, the strap 80 can be worn on two ears or on the head, so as to enable the face mask to be worn over the face of the user.

Conclusive from the above in accordance with the present invention, an air purification face mask structure for holding out air pollution, which has anti-bacterial, anti-inflammation and anti-oxidation effects.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. An air purification face mask structure, comprising:
   a body having an opening in a central part thereof and a discharge port respectively provided on two sides thereof;
   a fan mounted in the body;
   a filter coveringly provided at the opening of the body;
   an outer cover provided at a front end of the body;
   an air deflector engagingly fitted in the body, wherein the air deflector has an upper half portion thereof provided with a plurality of first guide holes, and a lower half portion thereof provided with a plurality of second guide holes;
   an ultrasonic vibration device mounted on the air deflector, comprising: a container, a circuit board and a nozzle, wherein the container is stored therein with an enzyme or essential oil, or a mixture of both, the circuit board has one end thereof electrically connected to the fan and another end thereof connected to a charging socket, the nozzle is mounted on the container and electrically connected to the circuit board, the nozzle is capable of atomizing a liquid in the container, so as to configured to the same towards the nose and the mouth of a user;
   a face mask body provided at a back end of the body, so that when the user wears the face mask, the face mask body being tightly fitted to the nose of the user; and
   a strap provided on the body for enabling the face mask to be worn over the face of the user.

2. The air purification face mask structure according to claim 1, wherein the plurality of first guide holes are slanted upwards to form an angle with a horizontal plane, when external air passes through the fan and is guided into the body, the air current being configured to the nose and the mouth of a face mask user for breathing.

* * * * *